(12) United States Patent
Lau et al.

(10) Patent No.: US 7,178,528 B2
(45) Date of Patent: Feb. 20, 2007

(54) HEADGEAR FOR NONINVASIVE VENTILATION INTERFACE

(76) Inventors: Greg Y. Lau, 155 Boyce Dr., Mocksville, NC (US) 27028; Christopher B. Reed, 155 Boyce Dr., Mocksville, NC (US) 27028

( * ) Notice: Subject to any disclaimer, the term of this patent is extended or adjusted under 35 U.S.C. 154(b) by 0 days.

(21) Appl. No.: 11/069,170

(22) Filed: Mar. 1, 2005

(65) Prior Publication Data

US 2006/0196511 A1  Sep. 7, 2006

(51) Int. Cl.
  *A61M 15/08* (2006.01)
  *A62B 7/00* (2006.01)
(52) U.S. Cl. .................. 128/207.18; 128/206.21; 128/206.24; 128/207.11; 128/206.28; 128/201.22; 128/206.26; 128/206.18; 128/206.11; 128/202.27; 128/206.27; 128/201.23; 128/201.29
(58) Field of Classification Search ........... 128/207.18, 128/200.24, DIG. 26, 206.21, 206.24, 207.11, 128/206.28, 201.22, 206.26, 206.18, 206.11, 128/202.27, 206.27, 201.23, 201.29
See application file for complete search history.

(56) References Cited

U.S. PATENT DOCUMENTS

| | | | | |
|---|---|---|---|---|
| 2,292,568 A | * | 8/1942 | Kanter et al. | 128/203.28 |
| 2,525,236 A | * | 10/1950 | Palmer | 128/205.25 |
| 2,617,415 A | * | 11/1952 | Rosen et al. | 128/206.28 |
| 3,156,923 A | * | 11/1964 | Walter | 2/419 |
| 3,441,020 A | * | 4/1969 | Aasen et al. | 128/205.25 |
| 3,683,907 A | * | 8/1972 | Cotabish | 128/200.28 |
| 3,955,570 A | * | 5/1976 | Hutter, III | 128/201.23 |
| 4,055,173 A | * | 10/1977 | Knab | 128/847 |
| 4,195,363 A | * | 4/1980 | Jenson | 2/8.6 |
| 4,593,688 A | * | 6/1986 | Payton | 128/200.28 |
| 4,774,946 A | * | 10/1988 | Ackerman et al. | 128/207.18 |
| 5,704,916 A | * | 1/1998 | Byrd | 604/179 |
| 6,119,694 A | * | 9/2000 | Correa et al. | 128/207.13 |
| 6,889,689 B1 | * | 5/2005 | Neuman | 128/201.22 |

\* cited by examiner

*Primary Examiner*—Henry Bennett
*Assistant Examiner*—Nihir Patel
(74) *Attorney, Agent, or Firm*—Gilbert J. Andia, Jr.

(57) ABSTRACT

The present invention is a headgear for noninvasive ventilation interface made up of a nasal cannula including cannula tubing having a given outside diameter, and a headgear yoke with ends including tubing retainers. The yoke is adapted to extend transversely over a wearer's head. The tubing retainers are C-shaped projections having a given length and an inside diameter substantially equal to the tubing outside diameter. The present invention further includes a retainer mating element for each of the C-shaped tubing retainers to prevent the tubing from kinking near the C-shaped tubing retainers. The retainer mating element has an elbow section with an open side and a clip section connected to the elbow section by a rigid beam having a length substantially equal to the C-shaped tubing retainer given length, wherein both of the sections have an inside diameter substantially equal to the tubing given outside diameter.

6 Claims, 4 Drawing Sheets

FIG. 2

HEADGEAR FOR NONINVASIVE VENTILATION INTERFACE

BACKGROUND OF THE INVENTION (1) Field of the Invention

The present invention relates to an adjustable, semi-rigid headgear for maintaining the proper positioning of a headgear for a noninvasive ventilation interface about a wearer's head and on the wearer's face. In particular, the present invention prevents the kinking of medical gas tubing and holds a nasal cannula in proper position as the wearer sleeps and/or changes their head's position.

(2) Description of the Prior Art

There are certain medical situations in which it is necessary or desirable to deliver a flow of breathing gas to the airway of a patient without intubating the patient or surgically inserting a tube in the patient's trachea. For example, a patient might be ventilated using a technique known as non-invasive ventilation. Non-invasive ventilation interfaces are also used with patients having a medical disorder such as sleep apnea who might require continuous positive airway pressure (CPAP) or Bilevel Positive Airway Pressure in which positive pressure is maintained during inspiration but reduced during expiration, and Intermittent Mechanical Positive Pressure Ventilation in which pressure is applied when an episode of apnea is sensed.

Such non-invasive ventilation and pressure support methodologies involve the placement of a patient non-invasive interface device, which is typically a nasal cannula or face mask or nasal pillows, on the face of a patient. The patient interface device communicates the flow of breathing gas from the ventilator or pressure support device with the airway of the patient, so that the therapeutic flow of breathing gas can be delivered from the pressure/flow generating device to the airway of the patient. It is known to maintain such interface devices on the face of a wearer by a headgear having upper and lower straps, each having opposite ends threaded through connecting elements provided on the opposite sides and, on some, the top of the interface device. Because such devices are typically worn for an extended period of time, it is important that the headgear maintain the device in a tight enough seal against a patient's face or nose without discomfort.

Persons with medical conditions such as lung disease or those recovering from surgery often require supplemental oxygen. Usually, the supplemental oxygen is delivered through medical gas tubing attached to a nasal cannula or medical gas mask. Generally, some fastening means is needed to properly hold the nasal cannula or medical gas mask properly against a wearer's face.

There are problems with typical headgear used with these interface devices. Many patients find the harness, headband, or other headgear used to keep the mask in position uncomfortable, particularly when sleeping. The headband or harness must typically maintain the interface device against the face or nose of the wearer with some pressure, resulting in significant patient discomfort and irritation.

Examples of prior art fastening means include fabric headbands and fabric harnesses that fasten about a wearer's head. U.S. Pat. No. 6,684,833 to Burns discloses an example of the fabric headband type. Burns teaches a nasal cannula headband apparatus in which medical gas tubing is attached to the outer side of the headband by fasteners that keep the cannula tubing in place relative to the headband and direct the cannula tubing behind the wearer's ears. While this type of headband apparatus may be adequate for some patients, others will no doubt find the headband too uncomfortable for long term use because of restriction to blood vessels in their forehead region. Moreover, Burns does not teach a means to prevent the cannula tubing from kinking caused by the wearer's movements. U.S. Pat. No. 6,119,694 to Correa et al. discloses a harness type mask as shown in FIG. 2 of the disclosure's drawings. As with Burns, some patients will find this type of tubing fastening apparatus to be too restrictive to be comfortable. Moreover, Correa et al does not disclose a means to direct medical gas tubing such that it does not kink as the wearer changes positions while sleeping, etc. What is needed is a medical tubing fastening apparatus that does not restrict blood flow in the wearer's forehead, while also providing a means to prevent the medical gas tubing from kinking as the wearer changes head positions.

Additionally, fabric or elastic headbands or headgear often become tangled and twisted, and are therefore difficult for the user to easily place on the user's head. Additionally, the prior art headgear are often tightened significantly about the wearer's head in order to maintain the interface device in proper position. Lastly, the prior art headgear causes significant difficulty in properly locating the interface device on the wearer and requires significant adjustment. Thus, what is needed is a headgear that is simpler to place on the wearer's head, that does not become twisted or entangled, and that requires minimal adjustment for proper placement of the interface device.

SUMMARY OF THE INVENTION

The present invention is directed to a headgear for non-invasive ventilation interface made up of a nasal cannula and tubing having a given outside diameter, and a headgear yoke with curved ends including tubing retainers. The yoke is adapted to extend transversely over a wearer's head and includes side sections with top and bottom ends and a top section connectable to the side section top ends. Preferably, the yoke is adjustable in length. For example, in one embodiment the headgear yoke includes spaced index notches near the top end of at least one of its side sections along with at least one side section receiving slot within the yoke top section. The yoke top section also includes at least one index notch lock having locking and unlocking positions usable to secure or release the at least one indexed side section. The sections of the headgear yoke are semi-rigid and lightweight. Suitable construction materials for the headgear yoke include, but are not limited to metal such as aluminum alloy and plastics such as polyvinyl chloride and nylon. Preferably, the headgear yoke sections are molded from a single type of material, but the yoke section could also be made of composite materials. For example, the yoke top section can be made from metal and the side sections rigid plastic or vice versa. The headgear yoke is semi-rigid in that the yoke is flexible and therefore is bendable and twistable, but is neither longitudinally elastic nor compressible.

The apparatus of the present invention also includes a length adjustable strap adapted to extend transversely behind the wearer's head. The strap has ends that are attachable to the headgear yoke at locations adjacent opposite sides of the wearer's head when the headgear yoke is extending transversely over the wearer's head. The strap has spaced index holes near both of the strap ends. The headgear yoke side sections include outwardly projecting studs that engage the strap's index holes in order to secure the strap to the headgear yoke. In one embodiment, the strap is made from a thin elongated plastic strip. However, the strap can be made from any durable flexible material. The studs can be mushroom shaped, or any other conventional shape to retain the strap to the yoke.

The tubing retainers are C-shaped outwardly projecting clips having a given length and an inside diameter substantially equal to the tubing outside diameter. It is preferred that the C-shaped tubing retainers be integrally formed with the yoke side section bottom ends. Therefore, if the yoke side sections are molded from a semi-rigid plastic, the C-shaped tubing retainers would also be made of the same semi-rigid plastic. The yoke side section bottom ends are preferably curved so that the C-shaped tubing retainers place the clips in a position forward of the wearer's ears.

A mating element for each of the C-shaped tubing retainers is included to prevent the tubing from kinking near the C-shaped tubing retainers. Each retainer mating element has an elbow section with an open side and a clip section connected to the elbow section by a rigid beam having a length substantially equal to the C-shaped retainer given length, wherein both of the sections have an inside diameter substantially equal to the tubing given outside diameter for receiving the tubing's outside diameter. These retainer mating elements are mateable with the C-shaped tubing retainers to capture and direct the tubing from in back of the wearer's head to along the sides of the wearer's face whenever the headgear yoke is worn extending transversely over the wearer's head. The tubing may be directed behind the wearer's head and downwardly, or behind the wearer's head and upwardly. Alternatively, the tubing may be directed downwardly but in front of the wearer' neck and chest.

In operation, the length of the headgear yoke is adjusted to comfortably fit transversely over a wearer's head. To adjust the length, the notch lock is placed in the unlocking position and the notched yoke side section is either moved a number of index notches inwardly or outwardly of the at least one side section receiving slot until a desired effective yoke length is achieved. Once the length of the yoke is appropriately adjusted, the notch lock is placed in the locking position to maintain the desired yoke length. Next the tubing of the nasal cannula is placed into the C-shaped tubing retainers such that the nasal cannula fits properly on the wearer's face. Then, the retainer mating elements are mated with the C-shaped tubing retainers to prevent the tubing from kinking near the C-shaped tubing retainers. In a first mating configuration, the elbow section of the retainer elements direct sections of the tubing in a direction that is adjacent the wearer's head and substantially parallel with each respective yoke side section. In second mating configuration, the elbow section of the retainer elements direct sections of the tubing in a direction that is adjacent the wearer's neck. The retainer element rigid beam section encloses the tubing within the C-shaped tubing retainer, and the retainer element clip section fastens over the tubing at the end of the rigid beam at a location just beyond the length of the C-shaped tubing retainer. Once the tubing is captured by the C-shaped tubing retainers and retainer element mated combination, the headgear yoke is placed transversely over the wearer's head. Next, the length adjustable strap adapted to extend transversely behind a wearer's head is positioned such that the index holes near the ends of the strap are engaged by the studs projecting from the yoke side sections to result in the strap having a desired effective length. The headgear yoke and strap will then hold the nasal cannula in place even as the wearer moves, such as movements during sleep.

DETAILED DESCRIPTION OF THE INVENTION

In the following description, terms such as horizontal, upright, vertical, above, below, beneath and the like are used solely for the purpose of clarity in illustrating the invention and should not be taken as words of limitation. The drawings are for the purpose of illustrating the invention and are not intended to be to scale.

Figure 1:
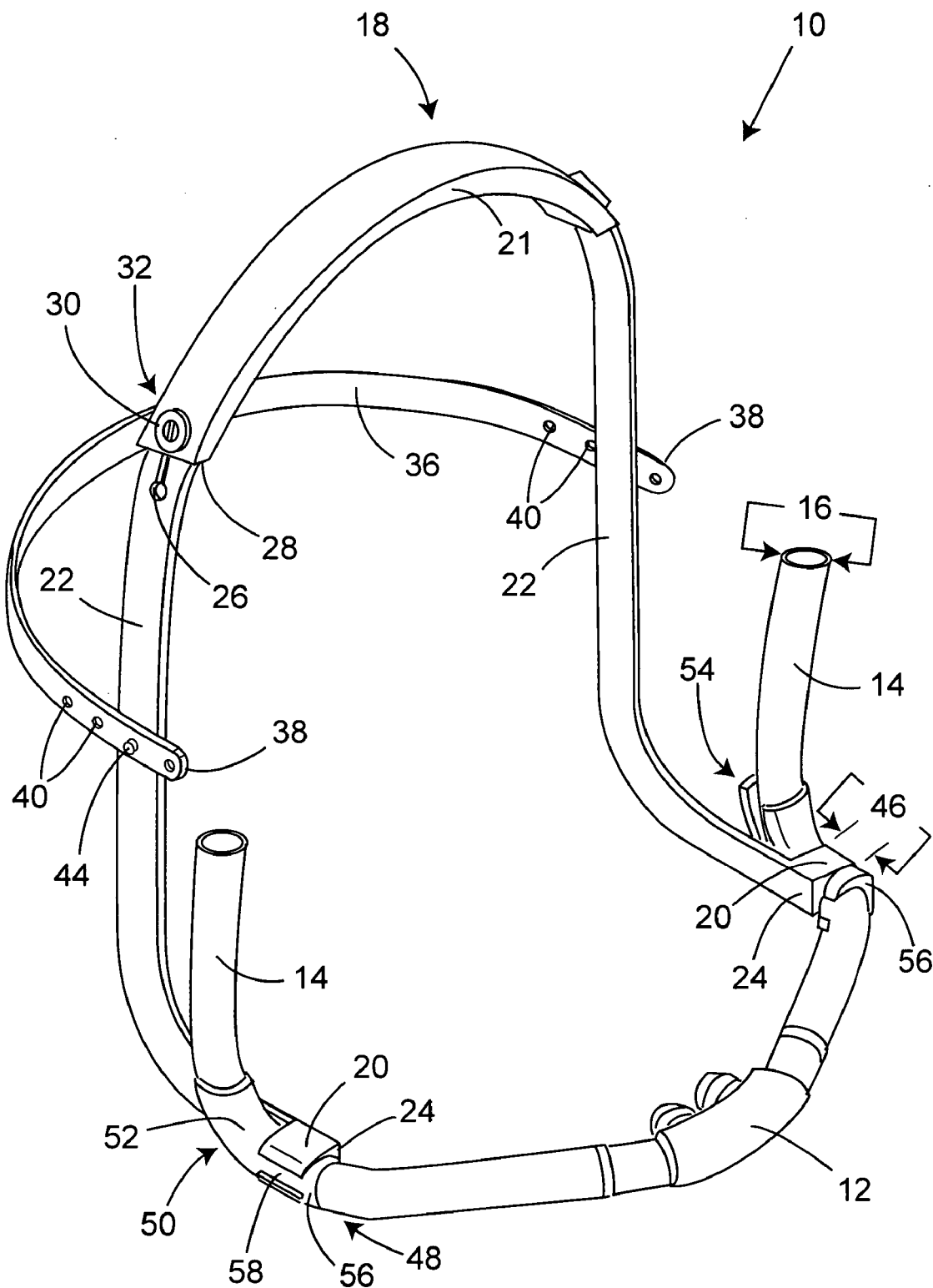
FIG. 1 is a perspective view of the medical gas delivery device with the C-shaped tubing retainers combined with the retainer mating elements in the first mating position.
Figure 2:
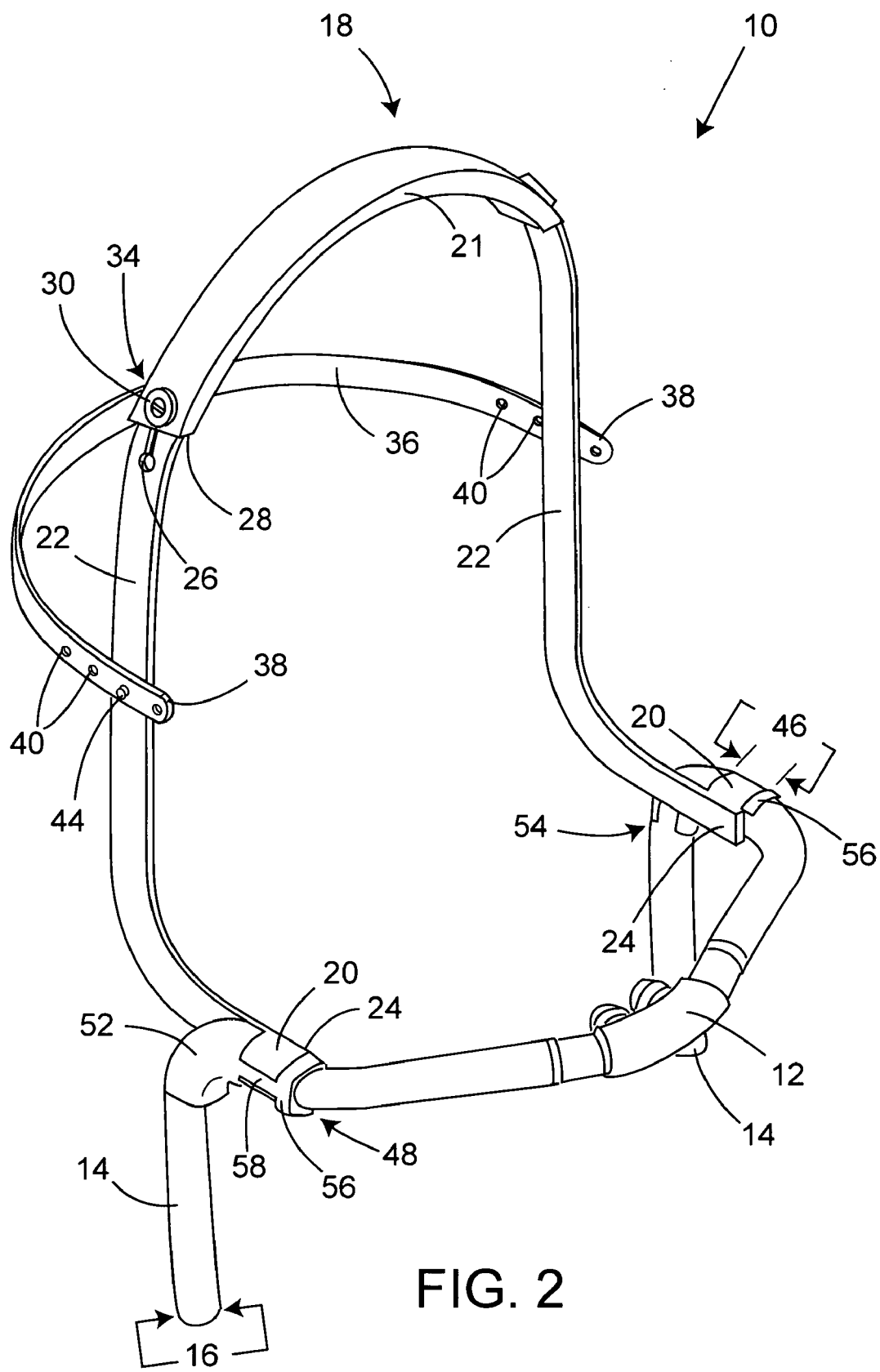
FIG. 2 is a perspective view of the medical gas delivery device with the C-shaped tubing retainers combined the retainer mating elements in the second mating position.

Referring to the drawings and first to FIGS. 1 and 2, a headgear for noninvasive ventilation interface 10, comprises a nasal cannula 12 including cannula tubing 14 having a given outside diameter 16; and a headgear yoke 18 with ends including cannula tubing retainers 20. In particular, headgear yoke 18 includes a top section 21 and side sections 22 with lower ends 24. Moreover, headgear yoke 18 includes spaced index notches 26 near the top end of at least one of its side sections 22 along with at least one side section receiving slot 28 within yoke top section 21. The yoke top section 21 also includes at least one index notch lock 30 having an unlocking position 32 shown in FIG. 1, and a locking position 34 shown in FIGS. 2 and 3. These positions are usable to secure or release the at least one indexed side section 22.

Headgear for noninvasive ventilation interface 10, further includes a length adjustable strap 36 adapted to extend transversely behind the wearer's head. Strap 36 has ends 38 attachable to yoke side sections 22 at locations adjacent opposite sides of the wearer's head when headgear yoke 18 is extending transversely over the wearer's head. Strap 36 has spaced index holes 40 near both of ends 38 of strap 36. The headgear yoke side sections 22 include outwardly projecting studs 44 that engage index holes 40 in order to secure strap 36 to headgear yoke 18.

Figures 3, 4:
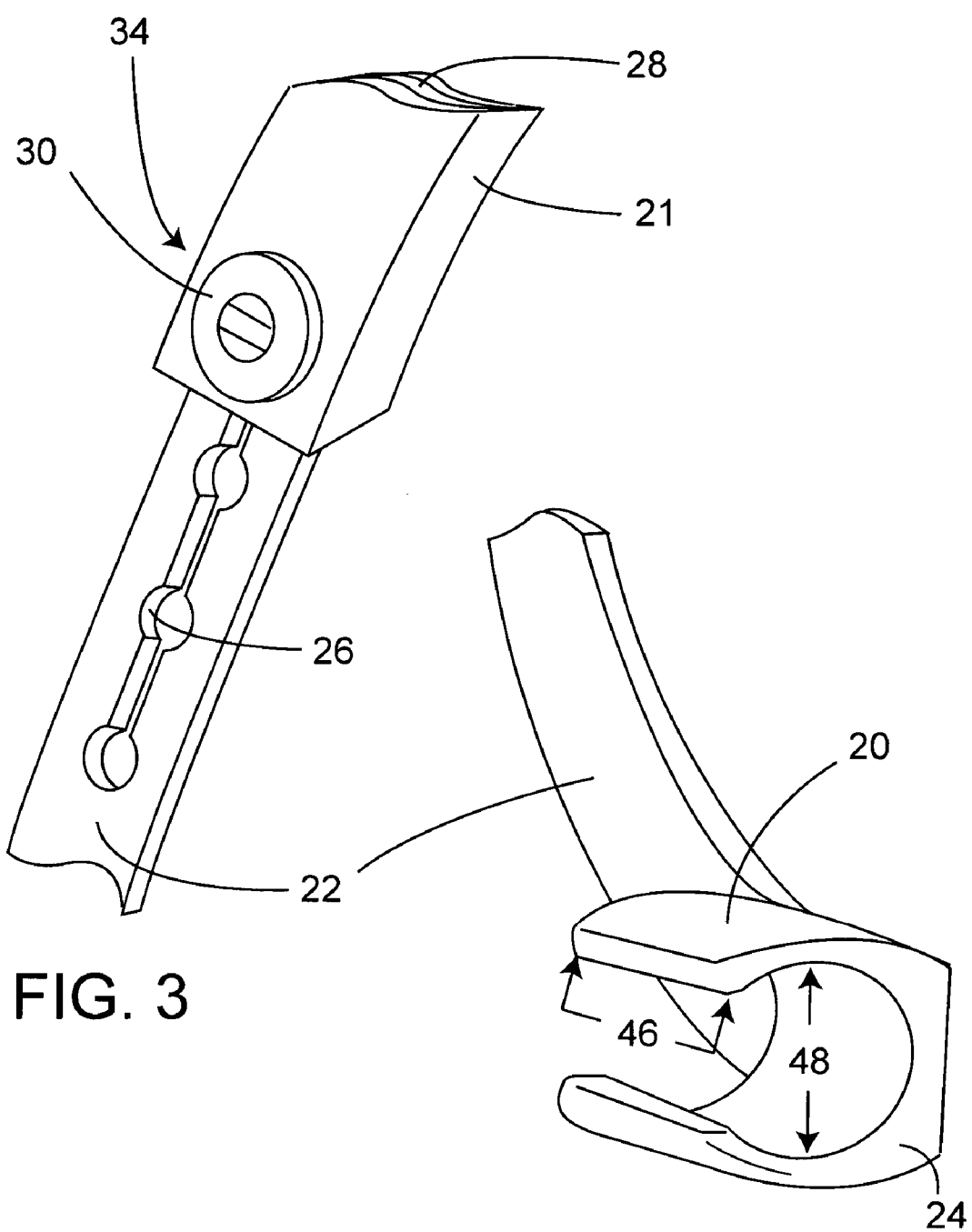
FIG. 3 is a close-up perspective view of the notch lock mechanism for adjusting the yoke length of the headgear.
FIG. 4 is a close-up perspective view of a C-shaped tubing retainer.
Figure 5:
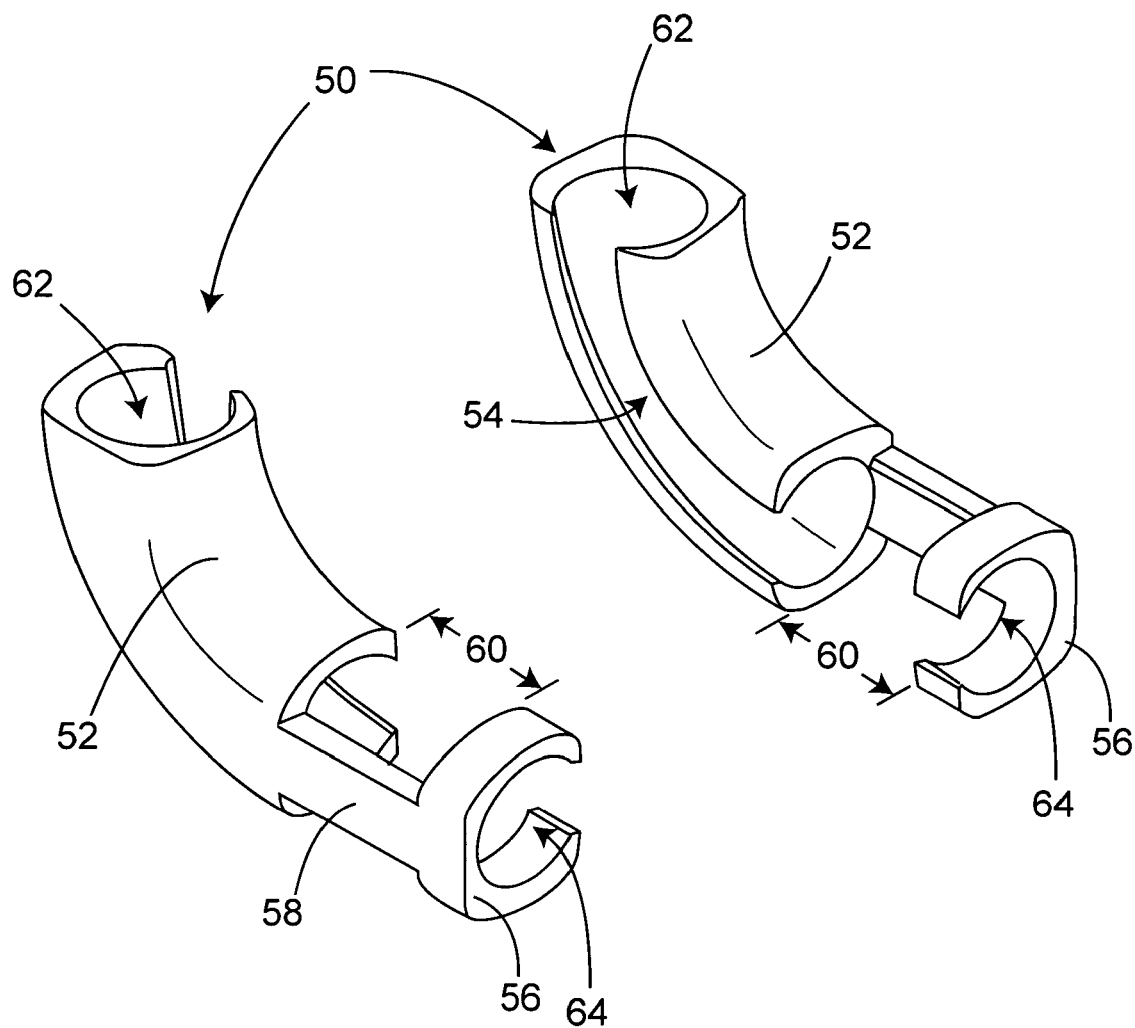
FIG. 5 is a perspective view of the retainer mating elements.

Cannula tubing retainers 20 are C-shaped outwardly projecting clips having a given length 46 and an inside diameter 48 substantially equal to the tubing outside diameter 16. A retainer mating element 50 for each of the C-shaped tubing retainers 20 is included to prevent the tubing from kinking near C-shaped tubing retainers 20. As best seen in FIG. 4, the retainer mating elements 50 have an elbow section 52 with an open side 54 and a clip section 56 connected to the elbow section 52 by a rigid beam 58 having a length 60 substantially equal to the C-shaped retainer given length 46, wherein both elbow section 52 and clip section 56 have an inside diameter 62 and 64, respectively that are substantially equal to tubing given outside diameter 16.

In operation, the length of headgear yoke 18 is adjusted to comfortably fit transversely over a wearer's head. To adjust the length, notch lock 30 is placed into unlocking position 32 and notched yoke side section 22 is either moved a number of index notches inwardly or outwardly of the at least one side section receiving slot 28 until a desired effective yoke length is achieved. Once the length of yoke 18 is appropriately adjusted, notch lock 30 is placed into locking position 34 to maintain the desired yoke length. Next, the tubing 14 is placed into the C-shaped clips such that the nasal cannula 12 fits properly on the wearer's face. Then, the retainer mating elements 50 are mated with C-shaped clips 20 to prevent the tubing from kinking near the C-shaped clips. Retainer elements 50 and C-shaped clips 20 are shown in FIG. 1 in the first mating position. In this position, elbow section 52 of retainer elements 50 direct sections of tubing 14 in a direction that is substantially parallel with yoke side sections 22. A retainer element rigid beam section 58 encloses tubing 14 within C-shaped clip 20, and retainer element clip 56 fastens over tubing 14 at the end of rigid beam 58 at a location just beyond the length of C-shaped clip 20. Once the tubing is captured by C-shaped clips 20 and retainer mating element 50, headgear yoke 18 is placed transversely over the wearer's head. Next, length adjustable strap 36 is positioned such that index holes 40 near strap ends 38 are engaged by studs 44 projecting from yoke side sections 22 to result in strap 36 having a desired effective length. Headgear yoke 18 and strap 36 will then maintain nasal cannula 12 in its proper position even as the wearer tosses and turns in their sleep.

Certain modifications and improvements will occur to those skilled in the art upon a reading of the description. It should be understood that all such modifications and improvements have been deleted herein for the sake of conciseness and readability but are within the scope of the following claims.

What is claimed is:

1. A headgear for maintaining the position of a noninvasive ventilation interface proximate to the nares of a patient comprising:
   a) a nasal cannula providing a seal with said nares including cannula tubing having a given outside diameter;
   b) a semi-rigid headgear yoke with a first and second side sections, said side sections having lower ends extending below the ears of said patient, said yoke being adapted to extend transversely over a wearer's head;
   c) cannula tubing retainers on said lower ends adapted for connection to said cannula tubing wherein said cannula tubing retainers are C-shaped projections having a given length and an inside diameter substantially equal to said cannula tubing outside diameter, and said projections are positioned in front of and below said patient's ears when worn, and
   d) further including a retainer mating element for each of said C-shaped retainers to prevent said cannula tubing from kinking near said C-shaped retainers, said retainer mating element having an elbow section with an open side and a clip section connected to said elbow section by a rigid beam having a length substantially equal to said C-shaped retainer given length, both of said sections having an inside diameter substantially equal to said tubing given outside diameter.

2. The headgear for maintaining the position of a noninvasive ventilation interface proximate to the nares of a patient of claim 1, wherein said C-shaped retainers and said retainer mating elements are mateable to capture and direct said cannula tubing to along the sides of the wearer's face whenever said headgear yoke is worn extending transversely over the wearer's head.

3. A headgear for supporting cannula tubing, and positioning a cannula in position to maintain a seal with the nares of a patient, said headgear comprising:
   a) a headgear yoke adapted to extend transversely over a wearer's head, said yoke having a top section and first and second side sections each having lower ends that when said headgear yoke is worn extend adjacent to opposite sides of the wearer's head;
   b) tubing retainers in the form of C-shaped clips integral with said lower ends for retaining and directing said cannula tubing to along the sides of the wearer's face and said C-shaped clips are positioned in front of and below a patient's ears when worn; and
   c) further including a retainer mating element for each of said C-shaped retainers to prevent said cannula tubing from kinking near said C-shaped retainers, said retainer mating element having an elbow section with an open side and a clip section connected to said elbow section by a rigid beam having a length substantially equal to said C-shaped retainer given length, both of said sections having an inside diameter substantially equal to said cannula tubing given outside diameter.

4. A headgear for noninvasive ventilation interface, comprising:
   a) a nasal cannula including cannula tubing having a given outside diameter;
   b) a semi-rigid headgear yoke with a first and second side sections, said side sections having lower ends, said yoke being adapted to extend fransversely over a wearer s head;
   c) C-shaped cannula tubing retainers on said lower ends having a given length and an inside diameter substantially equal to said cannula tubing outside diameter; and
   d) a retainer mating element for each of said C-shaped retainers to prevent said cannula tubing from kinking near said C-shaped retainers, said retainer mating element having an elbow section with an open side and a clip section connected to said elbow section by a rigid beam having a length substantially equal to said C-shaped retainer given length, both of said sections having an inside diameter substantially equal to said tubing given outside diameter.

5. The headgear for noninvasive ventilation interface of claim 4, wherein said C-shaped retainers and said retainer mating elements are mateable to capture and direct said cannula tubing to along the sides of the wearer's face whenever said headgear yoke is worn extending transversely over the wearer's head.

6. A headgear for supporting cannula tubing, said headgear comprising:
   a) a headgear yoke adapted to extend transversely over a wearer's head, said yoke having a top section and first and second side sections each having lower ends that when said headgear yoke is worn extend adjacent to opposite sides of the wearer's head;
   b) tubing retainers in the form of C-shaped clips integral with said lower ends for retaining and directing said cannula tubing to along the sides of the wearer's face, and
   c) a retainer mating element for each of said C-shaped retainers to prevent said cannula tubing from kinking near said C-shaped retainers, said retainer mating element having an elbow section with an open side and a clip section connected to said elbow section by a rigid beam having a length substantially equal to said C-shaped retainer given length, both of said sections having an inside diameter substantially equal to said cannula tubing given outside diameter.

* * * * *